(12) United States Patent
Villafranca

(10) Patent No.: US 11,523,775 B2
(45) Date of Patent: Dec. 13, 2022

(54) NON-INVASIVE HYDRATION AND ELECTROLYTE MONITORING

(71) Applicant: hDrop Technologies Inc., Little Rock, AR (US)

(72) Inventor: Adria Abella Villafranca, Little Rock, AR (US)

(73) Assignee: hDrop Technologies Inc., Little Rock, AR (US)

( * ) Notice: Subject to any disclaimer, the term of this patent is extended or adjusted under 35 U.S.C. 154(b) by 0 days.

(21) Appl. No.: 17/032,810

(22) Filed: Sep. 25, 2020

(65) Prior Publication Data

US 2021/0100501 A1  Apr. 8, 2021

Related U.S. Application Data

(60) Provisional application No. 62/910,165, filed on Oct. 3, 2019.

(51) Int. Cl.
*A61B 5/00* (2006.01)
*A61B 5/145* (2006.01)
(Continued)

(52) U.S. Cl.
CPC .......... *A61B 5/4875* (2013.01); *A61B 5/0022* (2013.01); *A61B 5/14546* (2013.01);
(Continued)

(58) Field of Classification Search
CPC ... A61B 5/443; A61B 5/4875; A61B 5/14546; A61B 5/1468; A61B 5/1477;
(Continued)

(56) References Cited

U.S. PATENT DOCUMENTS 3,399,666 A * 9/1968 Broach ................. G01N 27/07
600/372
4,765,179 A * 8/1988 Fuller .................... G01N 22/00
73/53.01
(Continued)

FOREIGN PATENT DOCUMENTS

JP  2009-115671 A  5/2009
JP  2016-138894 A  8/2016
(Continued)

OTHER PUBLICATIONS

Ortega, L., Llorella, A., Esquivel, J.P. et al. "Self-powered smart patch for sweat conductivity monitoring." Microsyst Nanoeng 5, 3 (2019). https://doi.org/10.1038/s41378-018-0043-0 (Year: 2019).*
(Continued)

*Primary Examiner* — Eric F Winakur
*Assistant Examiner* — Alice Ling Zou
(74) *Attorney, Agent, or Firm* — Dave Law Group LLC; Raj S. Dave

(57) ABSTRACT

A system for detecting salt ion concentration, comprising a device further comprising a sensor having a carbon printed electrode on a flexible substrate with adhesive on one side (backside) and the circuit electronics to generate pulse signal stimuli and measure salt concentrations to determine hydration level of a person or a living being, wherein the device is a wearable device. The electrode can be made into different shapes changing the area as necessary, since it is a carbon printed electrode and is flexible.

21 Claims, 8 Drawing Sheets

(51) Int. Cl.
 A61B 5/053 (2021.01)
 A61B 5/0531 (2021.01)
(52) U.S. Cl.
 CPC .......... *A61B 5/6802* (2013.01); *A61B 5/6832* (2013.01); *A61B 5/053* (2013.01); *A61B 5/0531* (2013.01); *A61B 2560/0204* (2013.01); *A61B 2562/164* (2013.01); *A61B 2562/227* (2013.01)
(58) Field of Classification Search
 CPC ..... A61B 5/681; A61B 5/6804; A61B 5/0002; A61B 55/14546; A61B 5/0531; A61B 5/0537; A61B 5/14517; A61B 5/4881; A61B 5/6801–6802; A61B 5/6831–6833; A61B 2562/0209–0214; A61B 2562/164–166; A61B 5/053–0533; A61B 5/2415; A61B 5/256; A61B 5/277; A61B 5/30; A61B 2560/0204; A61B 2560/0214; A61B 5/002; A61B 5/0024; G01N 27/026; G01N 27/028; G01N 27/02; G01N 27/048; G01N 27/045; G01N 27/121; G01N 27/122; G01N 27/125; G01N 27/223; G01N 27/30; G01N 27/308; G01N 27/333; G01N 27/4035
 See application file for complete search history.

(56) References Cited

U.S. PATENT DOCUMENTS

| | | | | |
|---|---|---|---|---|
| 4,966,158 | A * | 10/1990 | Honma | A61B 5/0531 324/692 |
| 7,383,072 | B2 * | 6/2008 | Edmonson | A61B 5/4266 600/362 |
| 7,783,344 | B2 * | 8/2010 | Lackey | A61B 5/6833 600/547 |
| 2002/0195623 | A1 | 12/2002 | Horiuchi | |
| 2005/0006234 | A1 * | 1/2005 | Hassibi | G01N 27/403 204/403.01 |
| 2013/0053673 | A1 * | 2/2013 | Brunswick | A61B 5/4266 600/384 |
| 2013/0274642 | A1 | 10/2013 | Soykan et al. | |
| 2014/0221792 | A1 * | 8/2014 | Miller | A61B 5/0537 600/309 |
| 2014/0275845 | A1 * | 9/2014 | Eagon | A61B 5/6826 600/301 |
| 2014/0318949 | A1 | 10/2014 | Wang et al. | |
| 2016/0066812 | A1 | 3/2016 | Cheng et al. | |
| 2017/0000415 | A1 * | 1/2017 | Lapetina | A61B 5/0205 |
| 2017/0325724 | A1 | 11/2017 | Wang et al. | |
| 2019/0001129 | A1 | 1/2019 | Rosenbluth et al. | |

FOREIGN PATENT DOCUMENTS

| | | | | |
|---|---|---|---|---|
| WO | WO-2007099522 | A2 * | 9/2007 | A61B 5/4854 |
| WO | WO-2009004001 | A1 * | 1/2009 | A61B 5/4266 |

OTHER PUBLICATIONS

Zhen Yuan, Lei Hou, Mallika Bariya, Hnin Yin Yin Nyein, Li-Chia Tai, Wenbo Ji, Lu Li, and Ali Javey. "A multi-modal sweat sensing patch for cross-verification of sweat rate, total ionic charge, and Na+ concentration" DOI: 10.1039/C9LC00598F (Paper) Lab Chip, 2019, 19, 3179-3189 (Year: 2019).*
G. Liu, K. Smith, T. Kaya, "Implementation of a microfluidic conductivity sensor—A potential sweat electrolyte sensing system for dehydration detection," 2014 36th Annual International Conference of the IEEE Engineering in Medicine and Biology Society, pp. 1678-1681, doi: 10.1109/EMBC.2014.6943929 (Year: 2014).*
International Search Report and Written Opinion dated Mar. 11, 2021 for PCT Application No. PCT/US2020/054334, 14 pages.

* cited by examiner

NON-INVASIVE HYDRATION AND ELECTROLYTE MONITORING

CROSS-REFERENCE TO RELATED APPLICATIONS

This application claims the benefit under 35 U.S.C § 119 of U.S. Provisional Application No. 62/910,165, filed on Oct. 7, 2019, which is hereby incorporated by reference in its entirety.

TECHNICAL FIELD

This invention relates to portable ion monitoring devices, and in particular, to topical monitoring of ion concentrations in body fluids.

BACKGROUND

Dehydration occurs when one uses or loses more fluid than you take in, and the body does not have enough water and other fluids to carry out its normal functions. If one does not replace lost fluids, they will get dehydrated. Anyone may become dehydrated, but the condition is especially dangerous for young children and older adults. The most common cause of dehydration in young children is severe diarrhea and vomiting. Older adults naturally have a lower volume of water in their bodies, and may have conditions or take medications that increase the risk of dehydration. This means that even minor illnesses, such as infections affecting the lungs or bladder, can result in dehydration in older adults.

Dehydration also can occur in any age group if you do not drink enough water during hot weather, especially when one is exercising vigorously. One can usually reverse mild to moderate dehydration by drinking more fluids, but severe dehydration needs immediate medical treatment.

Good hydration is essential for health and wellness. Every cell in the human body requires water. Hydration is central to the most basic physiological functions such as regulating blood pressure and body temperature, hydration, and digestion.

As dehydration increases, there is a gradual reduction in physical and mental performance. There is an increase in heart rate and body temperature, and an increased perception of how hard the exercise feels, especially when exercising in the heat. Studies show that loss of fluid equal to 2% of body mass is sufficient to cause a detectable decrease in performance (that is a 1.4 kg loss in a 70 kg athlete). Dehydration of greater than 2% loss of body weight increases the risk of nausea, vomiting, diarrhea, and other gastro-intestinal problems during exercise.

U.S. Patent Application Publication 20160338639A1 discloses various embodiments for a flexible hydration sensor that can be implemented in a wearable device. A hydration monitoring device can include at least one flexible electrode comprising a plurality of silver nanowires embedded within a polydimethylsiloxane (PDMS) substrate. Processing circuitry can be configured to measure a hydration level of an individual wearing the hydration monitoring device based at least in part on a measurement of a skin impedance of the individual. In some embodiments, the hydration monitoring device can also generate a hydration metric based on the level of hydration and display the hydration metric.

U.S. patent Ser. No. 10/092,203B2 discloses a wearable device including electrical contacts to detect voltages or other bio signals when mounted to the skin of a wearer. The impedance between a pair of the electrical contacts can be detected and the device operated based on the detected impedance. Such a detected impedance could be used to determine a physiological parameter, e.g., to determine a Galvanic skin response, a skin perfusion, a skin hydration level, or some other physiological parameters.

U.S. Pat. No. 8,734,341B2 discloses methods and apparatus to measure the hydration level of a user based on measuring the saliva of the user. A chemical compound is configured to change color of at least a portion of the water-permeable material due to contact with saliva and the change is observable from at least a portion of one piece of the water-impermeable material. The measurements are then used to indicate if the user is appropriately hydrated.

U.S. Pat. No. 7,783,344B2 discloses systems and techniques for monitoring hydration. In one implementation, the method includes measuring an electrical impedance of a region of a subject to generate an impedance measurement result, and wirelessly transmitting the data to a remote apparatus. The probe with which impedance is measured may take the form of a patch adhesively secured to the subject.

WO2016030869A1 discloses a wearable system based on an in-situ four-probe impedance measurement at different signal frequencies for the topical monitoring of at least one physiological parameter reflecting the hydration status such as skin conductivity, ion concentration in sweat or red blood cell characteristics. The said system is comprising a flexible substrate adapted to be directly or indirectly fixed to the skin and a plurality of conductive electrodes designed to be in contact with the body and to enable four-probe measurements of the bio-impedance of tissue and/or skin at one or more tissue site.

Skin impedance is a commonly used method in the cited prior arts to measure skin hydration level. The interpretation of skin impedance variations is not easy. First, it must be kept in mind that skin impedance is subject to sudden variations owing to internal or psychological factors; this is the well-known galvanic skin reflex (GSR). There is also a large site-to-site variation in individuals and the value in a given skin area is not steady the whole day nor is it from day to day. Furthermore, variations between individuals are enormous. The impedance between an electrical contact and skin and/or tissue beneath the skin could be related to a variety of factors of the skin, e.g., to a thickness of the skin, a fat content of the skin, a keratin content of the skin, a skin type (e.g., glabrous skin), a degree of moisture and/or hydration on/within the skin, a degree of perfusion of the skin, or some other properties of the skin. The impedance could change over time, e.g., the impedance could reduce over time due to accumulation of moisture (e.g., sweat, or other fluids) from the skin beneath and/or proximate an electrical contact mounted to the skin.

Currently, accurate and convenient, topical hydration monitoring devices, such as wearable hydration monitoring devices, are not readily available. While some wearable hydration monitoring devices have been developed, these devices are often inaccurate, difficult to clean, require invasive technologies, and are not reusable. Other monitoring devices have experienced difficulty with the skin interfering with the measurements and the inability to expose the sensor to a sufficient amount of bodily fluid for accurate hydration monitoring.

Therefore, there is a need for a device that can monitor the hydration of a living being in real time and for long periods of time using methods that reduce the interference of the input signal with output being measured along with the considering the influence of environment, factors specific to each living being such as weight, height, activity etc. in the living beings. More specifically, there is a need for a low power wearable or portable or a standalone device which is able to non-invasively evaluate and display in real time and for long periods a hydration level of a living being considering the influence of surrounding ambient conditions and factors specific to each living being.

SUMMARY

A device comprising, a sensor comprising a pair of electrodes on a flexible substrate; and an ion sensing circuit, wherein the sensor is electrically connected to the ion sensing circuit comprising a micro-controller that generates pulse signal stimuli, wherein the device is operable for detecting ion concentration in a fluid of a subject by the sensor.

A sensor comprising, a sensor comprising a pair of electrodes on a flexible substrate, and an ion sensing circuit comprising, a microcontroller, a pair of electrodes, at least a first resistor, a capacitor electrically connected in series with the at least a first resistor, at least a second resistor electrically connected in parallel with the pair of electrodes, a first node a reading node electrically connected to the first node, and a second node, wherein the first node is that which establishes a first electrical connection between the capacitor, and the parallel connection of the at least a second resistor and the pair of electrodes, wherein the second node is that which establishes a second electrical connection between the capacitor, and the parallel connection of the at least one second resistor and the pair of electrodes, wherein the sensor is electrically connected to the ion sensing circuit comprising a micro-controller that generates pulse signal stimuli, wherein the sensor is operable for detecting ion concentration in a fluid of a subject by the sensor.

A database comprising, conductivity information of at least one fluid of a subject, a real time ion concentration information of at the least one fluid obtained over a period of time, measurement information of at least one parameter of the subject, characteristic information of the subject, an environmental parameter that influences the reading of the sensor, a location data, a timestamp of when the measurements happened or taken, a physiological status of the subject and an index for data.

A method comprising, affixing a wearable device to a surface of a subject, providing excitation by applying pulsating direct current, pulsed at a predefined frequency, to a sensor through an energy source, determining in real time an ion concentration of a fluid over a period of time comprising at least a first reading and a second reading, communicating with a database the ion concentration of a fluid over the period of time; extracting physiological status information of the subject based on the difference between the first ion concentration and the second ion concentration, and displaying the physiological status information of the subject through at least one of a wearable device or a smart handheld device.

A system comprising, a sensor comprising, a pair of electrodes on a flexible substrate, and an ion sensing circuit comprising, a microcontroller, a pair of electrodes, at least a first resistor, a capacitor electrically connected in series with the at least a first resistor, at least a second resistor electrically connected in parallel with the pair of electrodes, a first node a reading node electrically connected to the first node and a second node, wherein the first node is that which establishes a first electrical connection between the capacitor, and the parallel connection of the at least a second resistor and the pair of electrodes, wherein the second node is that which establishes a second electrical connection between the capacitor, and the parallel connection of the at least one second resistor and the pair of electrodes, wherein the sensor is electrically connected to the ion sensing circuit comprising a micro-controller that generates pulse signal stimuli, wherein the sensor is operable for detecting ion concentration in a fluid of a subject by the sensor, wherein the system comprises of at least a processor, a memory in communication with the processor, a communication module, a display and a database where the sensor and system communicate through wireless communication means.

BRIEF DISCUSSION OF THE DRAWINGS

In the present disclosure, reference is made to the accompanying drawings, which form a part hereof. In the drawings, similar symbols typically identify similar components, unless context dictates otherwise. Various embodiments described in the detailed description, drawings, and claims are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein. The embodiments are illustrated by way of example and not limitation in the figures of the accompanying drawings, in which like references indicate similar elements and in which:

Reference will now be made to the attached drawings, when read in combination with the following detailed description, wherein like reference numerals refer to like parts throughout the several views, and in which.

DETAILED DESCRIPTION

Figure 1A:
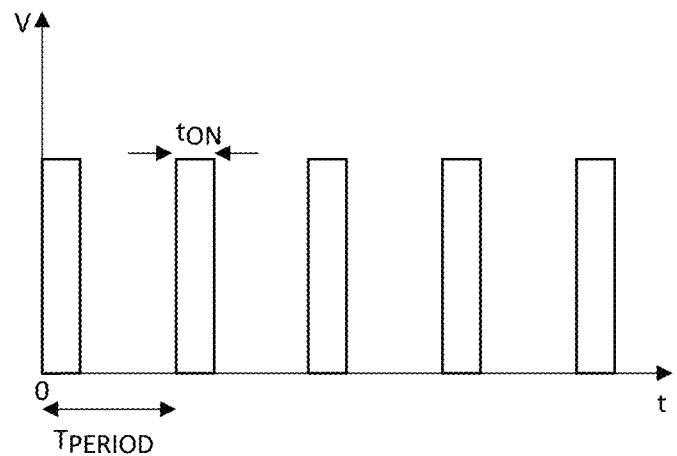
FIG. 1a depicts a pulse which may be used in the present invention according to an embodiment.

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a sensor" includes a plurality of such sensors.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open-ended term in this written description, like "comprising" or "including," it is understood that direct support should also be afforded to "consisting essentially of" language as well as "consisting of" language as if stated explicitly and vice versa.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. Occurrences of the phrase "in one embodiment," or "in one aspect," herein do not necessarily all refer to the same embodiment or aspect.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

Objects or structures described herein as being "adjacent to" each other may be in physical contact with each other, in close proximity to each other, or in the same general region or area as each other, as appropriate for the context in which the phrase is used.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter affecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, for example without limitation, a PLC (Programmable Logic Controller), an FPGA (field programmable gate array), an ASIC (application specific integrated circuit), Program-specific Standard Products (ASSPs), System-on-a-chip systems (SOCs), Complex Programmable Logic Devices (CPLDs), etc.

Processors suitable for the execution of a computer program include, by way of example, both general and special purpose microprocessors, and any one or more processors of any appropriate kind of digital computer. Generally, a processor will receive instructions and data from a read only memory or a random-access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a Web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

Embodiments of the present invention may comprise or utilize a special purpose or general-purpose computer including computer hardware. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network, such as a 5G network, or another communications connection (either hardwired, wireless, or a combination of hardwired or wireless) to a computer, the computer properly views the connection as a transmission medium. Transmission media can include a network and/or data links which can be used to carry data or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

As used herein, the term "Electrodes" represents an electrical conductor which is used to make contact with a non-metallic part of a circuit.

As used herein, the term "Control and measurement circuitry" represents a control and measurement circuitry that is a component of the overall system that contains the microprocessor and the sensor circuits connected to the microprocessor.

As used herein, the term "Temperature sensor" represents a device, typically, a thermocouple, RTD (resistance temperature detectors) or thermistor that provides for temperature measurement through an electrical signal.

As used herein, the term "Radio circuit" represents a circuit that provides wireless transmissions and includes a microprocessor to administer the inputs and outputs of the system. The radio circuit contains an antenna.

As used herein, the term "Antenna" represents the interface between radio waves propagating through space and electric currents moving in metal conductors, used with a transmitter or receiver.

As used herein, the term "Substrate" represents a type of material that supports the ion monitoring device. In one embodiment, the substrate is flexible to adapt to the contours of a surface. An example of a flexible substrate is Poly-Ethylene Terephthalate Glycol (PETG).

As used herein, the term "Energy source" represents a source from which useful energy can be extracted or recovered either directly or by means of a conversion or transformation process. An example includes a battery, which is a form of energy source that is used in the present invention according to an embodiment.

As used herein, the term "Smart hub" represents a smartphone, smart watch or any other personal mobile device that can connect wireless to a data transmitter.

As used herein, the term "body fluid" represents any fluid produced by a living organism, for example, interstitial fluids, saliva, tears, sweat and gastric juices.

As used herein, the term "App" represents an Application software either for mobile or computer.

As used herein, the term "in real time" or "real time" means relating to a system in which input data is processed within milliseconds so that it is available virtually immediately as an output or feedback to the process from which it is coming. The graphs or feedback is used to observe subjects in real time and display the resultant Ex: Room Air Conditioner which displays room temperature in real time, Electric Power System which measure and control power quality parameters like Frequency, Peak Voltage, Power Factor in real time, Real time ECG output etc.

An initial overview of technology embodiments is provided below, and specific technology embodiments are then described in further detail. This initial summary is intended to aid readers in understanding the technology more quickly but is not intended to identify key or essential technological features, nor is it intended to limit the scope of the claimed subject matter.

The embodiments herein and the various features and advantageous details thereof are explained more fully with reference to the non-limiting embodiments that are illustrated in the accompanying drawings and detailed in the following description.

The present invention offers advantages including but not limited to the following:

With the addition of components, such as a temperature sensor, the system is also able to perform a multi-parameter measurement. The cross analysis of multiple parameters may also allow the device to provide the exact dehydration level of a user or other parameters, for example an electrolyte related illness.

The system, with the addition of components, such a temperature sensor, is also able to measure the electrolytes of any liquid. This also allows to study and gather data of the electrolyte levels of other living and non-living creatures, plants, or liquids.

The system is non-invasive and requires no or minimal knowledge of the user to be operated.

The system can wirelessly communicate with a personal portable hub serving as a display interface through wireless connectivity such as Bluetooth, Wi-Fi, RFID, BLE, Radio Frequency Signal, GSM signal between others.

The proposed system is used to non-invasively evaluate in real time the hydration level of a person and extended for other applications, such as glucose levels, by exploiting the sweat resistance over a current measurement.

The data measured by the system may be advantageously wirelessly collected by a smart hub (smart phone, smart watch, or any other personal mobile device) that can perform more complex signal processing and serve as interactive display interface with an end-user.

The invention will be better understood below with some examples. It is worth noting that such examples are used only to illustrate certain forms of the applications of the invention, which are much broader and of more general purpose, for any applications where related to the non-invasive measurement of the ionic content of bio-fluids and their volume. In one embodiment, the ions being measured are electrolytes and the bio-fluid is sweat. Dehydration is directly related to the ion concentration in sweat.

FIG. 1a depicts a pulse which may be used in the present invention according to an embodiment. A pulse shape is formed by a rapid or sudden transient change from a baseline value to a higher or lower level value, which returns to the same baseline value after a certain time period. Such a signal can be termed as Pulse Signal. A pulse signal is a unidirectional, non-sinusoidal signal which is similar to a square signal, but it is not symmetrical like a square wave. A series of continuous pulse signals is simply called a pulse train. A train of pulses indicate a sudden high level and a sudden low-level transition from a baseline level which can be understood as ON/OFF respectively. Measurement from any point on one cycle to the same point on the next cycle is called the period of a wave form.

Figure 1B:
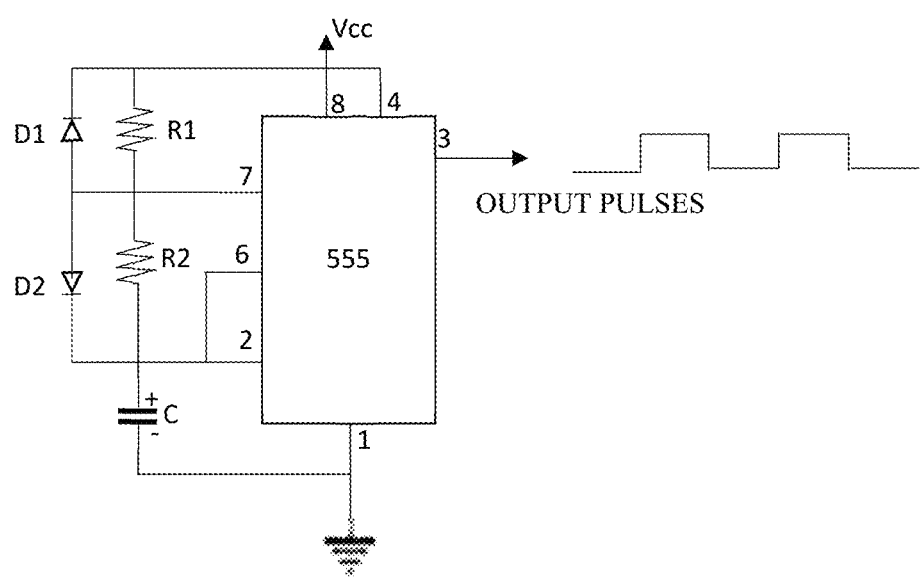
FIG. 1b depicts a circuit for pulse generation which may be used in the present invention according to an embodiment.

FIG. 1B depicts a circuit for pulse generation which may be used in the present invention according to an embodiment. An integrated circuit, which is most widely used for such purpose, is the 555 timer. This timer can be connected to operate as an oscillator (a stable multivibrator) as shown in FIG. 1B. The ON time of the generated pulse waveform, $t_{ON}$, is dependent on resistor R1, and is given by Equation (1):

$$t_{ON}=1169.0C_1R_1 \quad \text{Equation (1)}$$

During the ON period, diode D2 is forward biased and therefore resistor R2 is shorted. On the other hand, the OFF time, $t_{OFF}$, is dependent solely on resistor R2, and is given by Equation (2):

$$t_{OFF}=0.69.0C_1R_2 \quad \text{Equation (2)}$$

During the OFF period, diode D1 is forward biased and therefore resistor R1 is shorted. The period of the generated pulse waveform is shown in Equation (3):

$$T=t_{ON}+t_{OFF} \quad \text{Equation (3)}$$

In order to change the pulse width of the output signal of the timer, resistor R1 can be changed by connecting it as a potentiometer.

Figure 2A:
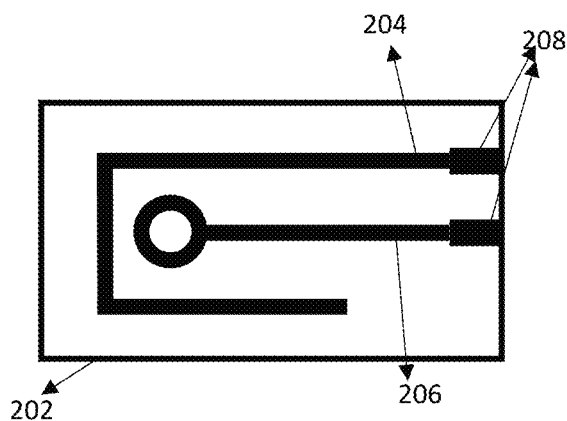
FIG. 2a depicts the top view of an electrode that may be used in the present invention according to an embodiment.
Figure 2B:
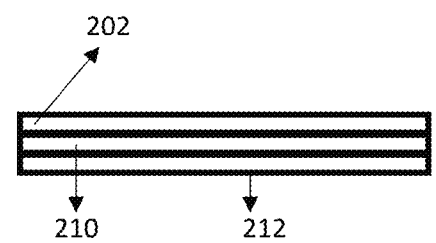
FIG. 2b depicts the side view of an electrode that may be used in the present invention according to an embodiment.

FIG. 2a and FIG. 2b depicts the top view and side view respectively of an electrode that may be used in the present invention according to an embodiment. Referring to the drawing for representative examples of the present invention, FIG. 2a is directed to a two-dimensional, planar circuit 202 used in the present invention according to an embodiment, comprising an electrode 204 and an electrode 206 forming a pair of electrodes. Also, shown are the leads 208 where the circuit will be connected to the electrode by zero force connectors or slider connectors. The two-dimensional planar structure when seen from the side view is as shown in FIG. 2b. It has three layers, first or top layer 202 is made of PET approximately 3 mils and is white in color on which the electrodes are printed with screen-printed electrodes (SPE) ink, next layer (second layer) 210, which is made of acrylic glue approximately 2 mils thick and the bottom or third layer, 212, which is a glue liner that can be peeled off before use. The first layer comprising electrodes, also referred to as electrode layer 202, is to rest on the skin of a person or living being wearing the device and in contact with the sweat of the person or living being while in use. The third layer, 212 can be peeled off and can be used for sticking easily to any surface such as a watch strap. All the three layers 202, 210 and 212 are referred to, in general, as an electrode. The thin and flexible electrode construction enables it to take the contour of the surface on which the electrode is stuck or glued.

The black portion or electrodes as shown as 204 and 206 represents the area of the electrodes and the gap between the electrodes 204 and 206 represents the distance between the electrodes. The voltage drop generated due to electrolyte sensing is a function of the area of the electrodes and the distance between the electrodes. The device is initially calibrated for sensing the electrolyte based on its area of the electrodes and the distance between the electrodes. In an embodiment, the limits of the area and distance between the electrodes may be varied. In the current embodiment of the invention, the area can vary between 10 $mm^2$ to 75 $mm^2$.

Figure 3:
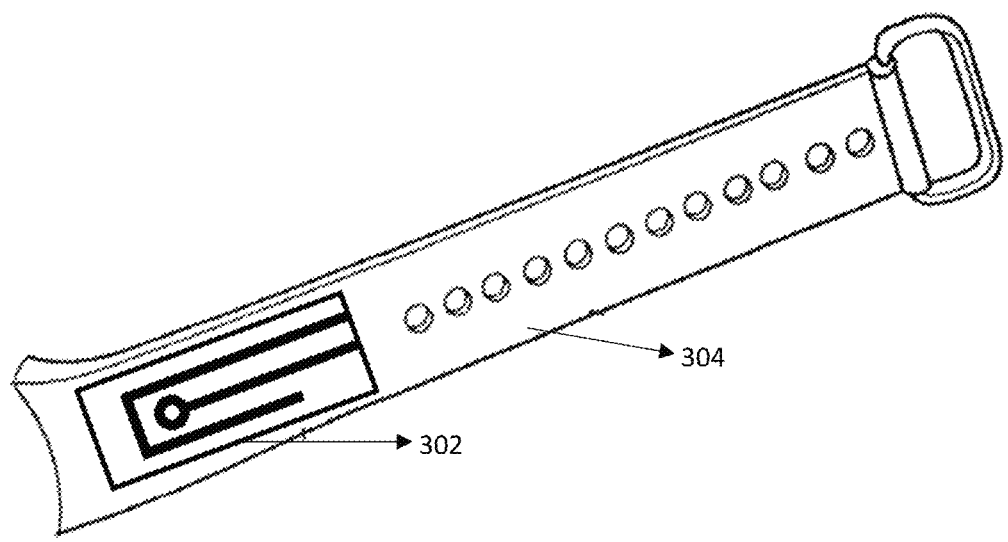
FIG. 3 depicts a hydration monitoring device with electrode as a wearable affixed to a band of a wearable device according to an embodiment.

FIG. 3 depicts a hydration monitoring device with electrode as a wearable affixed to a band of a wearable device according to an embodiment. It illustrates the device 302 (which is the same as 202 of FIG. 2), as part of a wearable or portable device 304. The device is attached to or is made as a part of the band 304 according to an embodiment. The device may also include an indicator. The indicator can be anything that communicates with the wearer, including, but not limited to a visual indicator, such as color, number, noise, vibration, or the like that communicates information to the wearer.

Regarding the circuit for pulsing the signal, pulse width modulation for a pulse signal of 200 hz maximum, similar to Integrated Circuits (IC) and timer ICs, an electromechanical switch or relay, transistor or any other switch mechanism to generate a pulse signal of the frequency specified in the patent.

Figure 4:
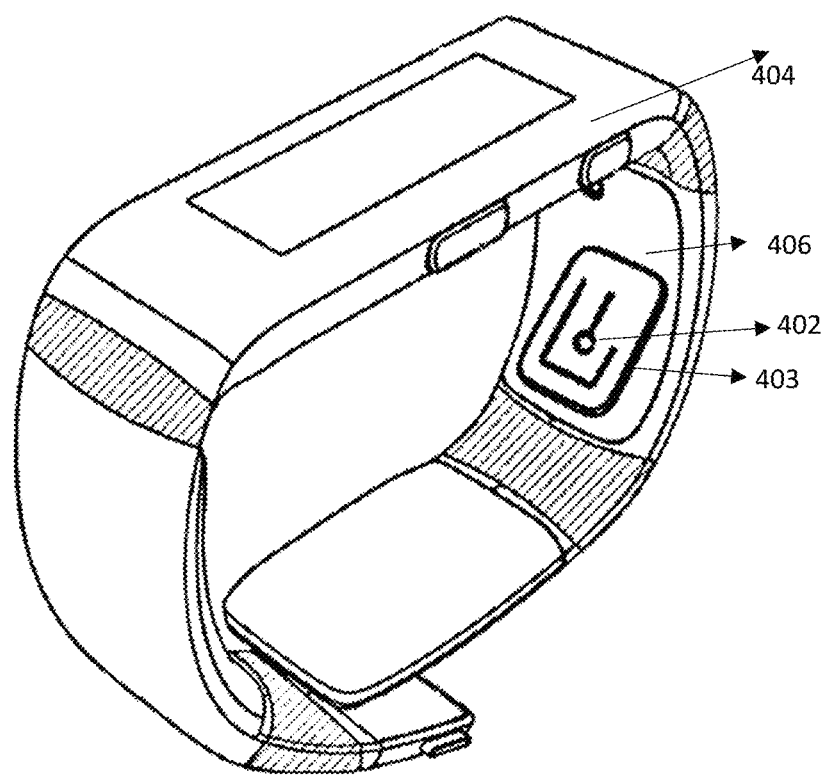
FIG. 4 depicts a hydration monitoring device as a wearable affixed to the band of a wearable device having a display according to an embodiment.

FIG. 4 depicts a hydration monitoring device as a wearable affixed to the band of a wearable device having a display according to an embodiment. FIG. 4 is a representation of a wearable device, a watch in this embodiment, which includes electrolyte measuring device or sensor 406 comprising an electrode 402 (also 302, 202) along with a microcontroller circuit 403, that is positioned such that the electrode can be exposed to a bodily fluid, such as sweat. In some embodiments, the microcontroller circuit 403 can be a part of the watch casing 404 in which case the electrode 402 can only be exposed on the wearable watch strap. The display of the device can be used to display the graphs, data or like from the device or sensor 406 via Bluetooth® or any near field communication method.

Figure 5:
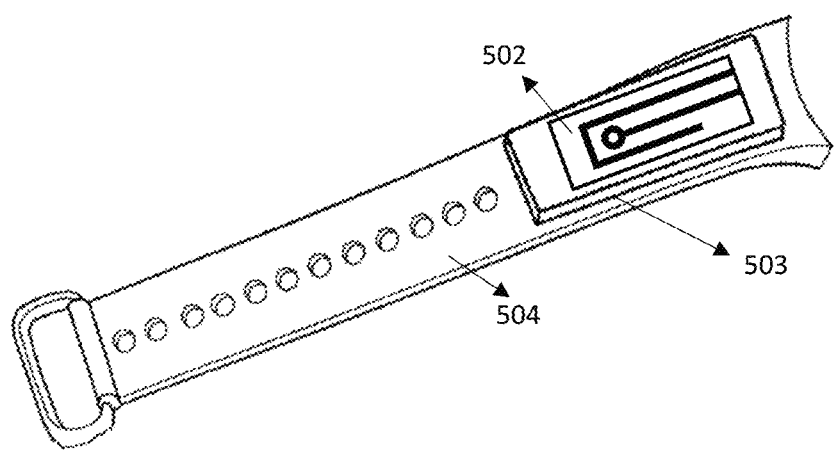
FIG. 5 depicts a band having a hydration monitoring device affixed thereto, so that the electrode of the device is in contact with the skin of the wearer of the band according to an embodiment.

FIG. 5 depicts a band having a hydration monitoring device affixed thereto, so that the electrode of the device is in contact with the skin of the wearer of the band according to an embodiment. An illustrative representation of a device 503 (also 403) with an electrode 502 (also 402, 302, 202) attached to a band 504 that can be worn by a person, such as an athlete during activity is shown according to an embodiment. In one of the embodiments, it is contemplated to put all the circuitry inside of a wearable device such as a watch. The circuitry and electrode can communicate through Bluetooth®. In another embodiment, the user can use a watch strap that has all the sensors and circuitry that can be attached to any wearable device such as a watch. Such watch straps with the embedded device can be sold as an independent product that can be used in combination with any watch of the user's choice. FIG. 3, FIG. 4, and FIG. 5 are different embodiments of the sensor and device. In FIG. 3 electrode is only shown, FIG. 4 shows electrode with circuit forming a sensor in a watch and FIG. 4 shows electrode with circuit forming a sensor in a strap. All these embodiments show that the electrode and circuit may or may not be in contact with each other but still form a sensor. It is referred to as a sensor when both sensor and electrode are present in a device but not necessarily juxtaposed or in contact physically with each other.

Figure 6:
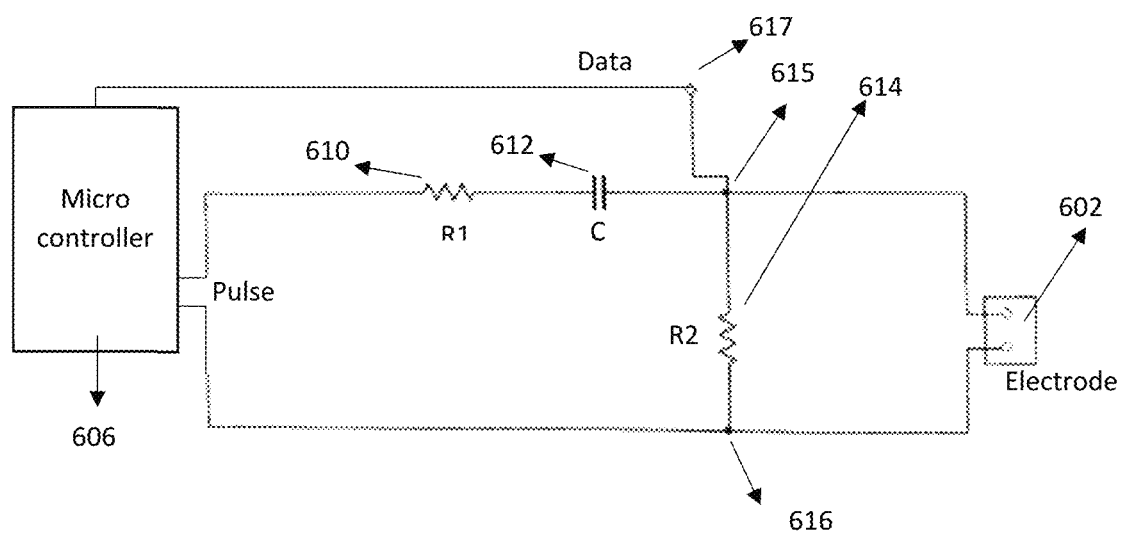
FIG. 6 is a schematic of a circuit of the sensor used in the present invention according to an embodiment.

FIG. 6 is a schematic of a circuit of the sensor used in the present invention according to an embodiment, in which the microcontroller 606 includes an energy source, such as a battery and is pulsing a signal to the electrode 602 as described in FIG. 1a and FIG. 1B. A voltage is applied to the circuit that can sense a change in ion concentration. The ion sensing circuit comprises, a pair of electrodes 602, a first resistor R1 shown as 610, a capacitor C shown as 612 electrically connected in series with the resistor R1, a second resistor R2 shown as 614 electrically connected in parallel with the pair of electrodes shown as 602. A first node, 615, establishes a first electrical connection between the capacitor, and the parallel connection of the second resistor and the pair of electrodes and a second node, 616, establishes a second electrical connection between the capacitor, and the parallel connection of the at least one second resistor and the pair of electrodes. A reading node, 617, is electrically connected to the first node and is operable to transfer all the data and readings to a processor or memory or a display device as configured.

Figures 7A, 7B:
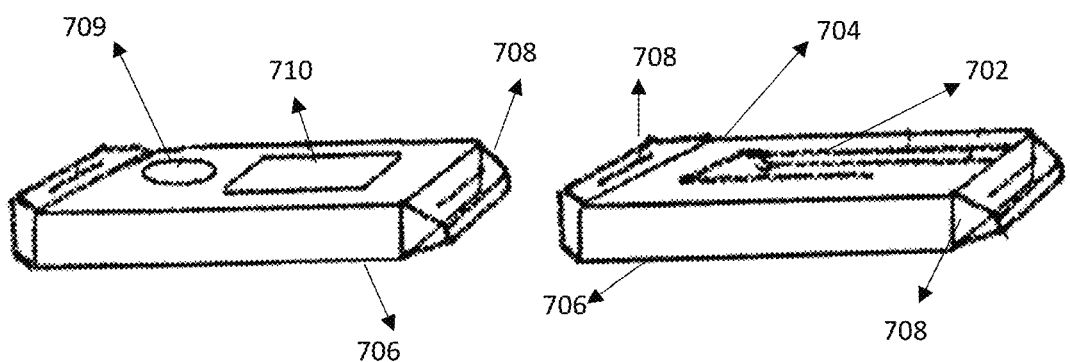
FIG. 7a depicts a bottom view of a hydration monitoring device or sensor wherein the device has a flat horizontal construction according to an embodiment.
FIG. 7b depicts the top view of a hydration monitoring device or sensor wherein the device has a flat horizontal construction according to an embodiment.

FIG. 7a and FIG. 7b depicts bottom view and top view respectively of a hydration monitoring device or sensor wherein the device has a flat horizontal construction according to an embodiment. As shown, the device or sensor 706 comprises an attachment 708 that can be used to attach the device or sensor 706 to other portable or wearable devices. The device or sensor 706 has an electrode 702, a microcircuit or a circuit 710, a battery holder 709 in housing 704 of the device or sensor 706.

In an embodiment, the device can be a part of a wearable, it can be embedded into the neck collar, it can be embedded in a sock, or into any piece of clothing.

Figure 8:
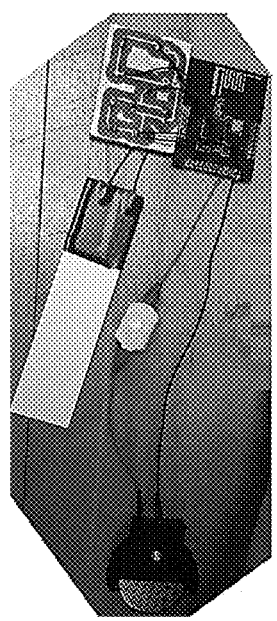
FIG. 8 depicts the inside of a hydration monitoring device showing the electronics and circuit connected to the electrode according to an embodiment.

FIG. 8 depicts the inside of a hydration monitoring device showing the electronics and circuit connected to the electrode according to an embodiment. The electronics and circuit are enclosed in a casing and are connected to the electrodes.

Figure 9A:
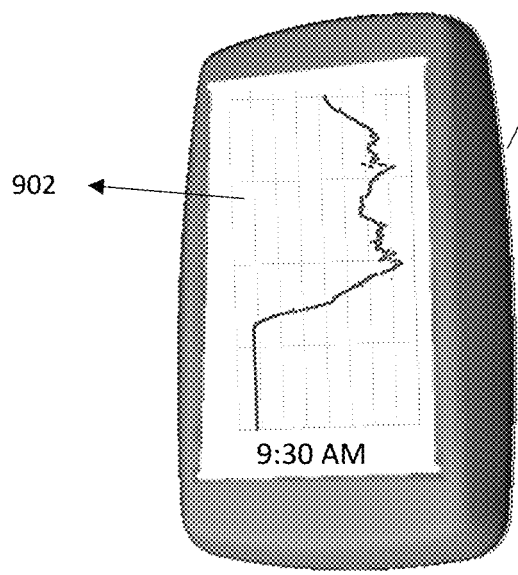
FIG. 9a depicts a stand-alone hydration monitoring device with an integrated display according to an embodiment.
Figure 9B:
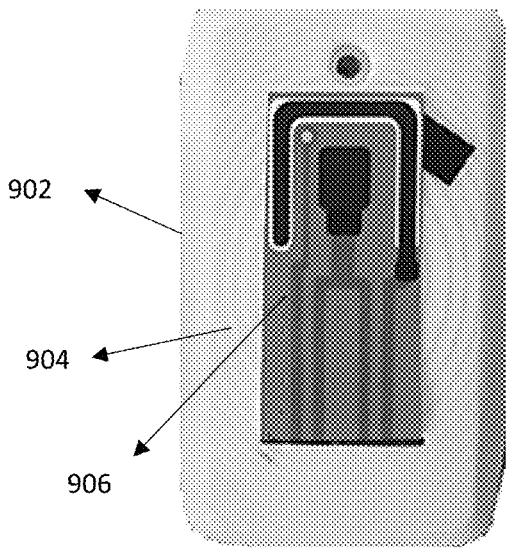
FIG. 9b depicts the back side of a stand-alone hydration monitoring device with an integrated display according to an embodiment.

FIG. 9a depicts a stand-alone hydration monitoring device with an integrated display according to an embodiment and FIG. 9b depicts the back side of a stand-alone hydration monitoring device with an integrated display according to an embodiment. A hydration monitoring device or sensor has an electrode towards the back side depicted as 904 and an integrated display 902 on the other side or front side which can be used to monitor the parameters when the device is used without any additional wearable devices such as watch. The device may be affixed to a sleeve according to an embodiment in such a way that the electrodes 906 present on the side of 904 are exposed and in touch with the user's skin. The device or sensor shows a graph of a sample workout session with hydration level monitoring is shown in FIG. 9a. The device, in this embodiment, can provide display of the monitored or calculated parameters including hydration in real-time without any additional device for visualization or data reading. Even when there is no integrated display, the device is still stand alone, capable of reading and storing the parameters except an additional display is needed to be connected for visualization of the data. The data is stored within the processor memory and can be accessible and visualized with data transfer to nearby devices having display.

Although the electrolyte monitoring device may be attached to the body or worn as a wearable, the detection device may also be for any body fluid or other fluid that contains electrolytes, such as urine or even with the vapor from plants.

The device may also include other elements including, but not limited to a temperature sensor, radio circuit, antenna, flexible substrate, an energy source. The device may also be part of a system. The device may also be part of a system that may include a remote sensor and a smart hub.

Conductivity is the measurement of the ions, such as electrolytes in a solution, such as perspiration. Conductivity is used to monitor the electrolytes in the body fluid. Conductance is the ability of the solution to conduct electric current. Conductance allows for the measurement of electrolytes in perspiration which can be used to determine the hydration status of a user. Conductance is related to resistance by using Equation (4).

$$R = \rho \frac{L}{A} \Omega \qquad \text{Equation (4)}$$

When the device is a wearable device or used with a wearable device to monitor hydration, the device can be safely placed on top of the skin of a subject. The current is minimal, about 0-0.01 Amperes, allowing the device to contact the skin without harm or discomfort. The user's body, such as skin and body hair, may impact the resistance. The resistance of the user's body may vary depending upon the points of contact and the skin condition. Skin can be moist or dry. The skin resistance may vary from approximately 1000 ohms for wet skin to over 500,000 ohms for dry skin. The device according to the present invention uses a direct current and more particularly direct current pulsing system.

An example of the device claimed in the present invention was designed in SolidWorks® and 3D printed in glycol modified polyethylene terephthalate (PETG). The hardware casing of the design can be any wearable technology applied material. The ion sensing circuit 202 (also 302, 402, 702) reads the electrolyte conductivity of sweat in real time by using a circuit comprising resistors 610, 614, at least one capacitor 612, and a voltage source to a microcontroller or a microprocessor 606. Sweat is composed of ions that conduct electricity, by using this ion sensing device comprising an ion sensing circuit 202 (also 302, 402, 702), the voltage differential between at least two electrodes can be determined under a pulsating direct current. To establish a relationship between the voltage differential and electrolyte concentration in sweat, controlled correlations were generated using artificial sweat in different concentrations and measuring the voltage drop.

Figure 10:
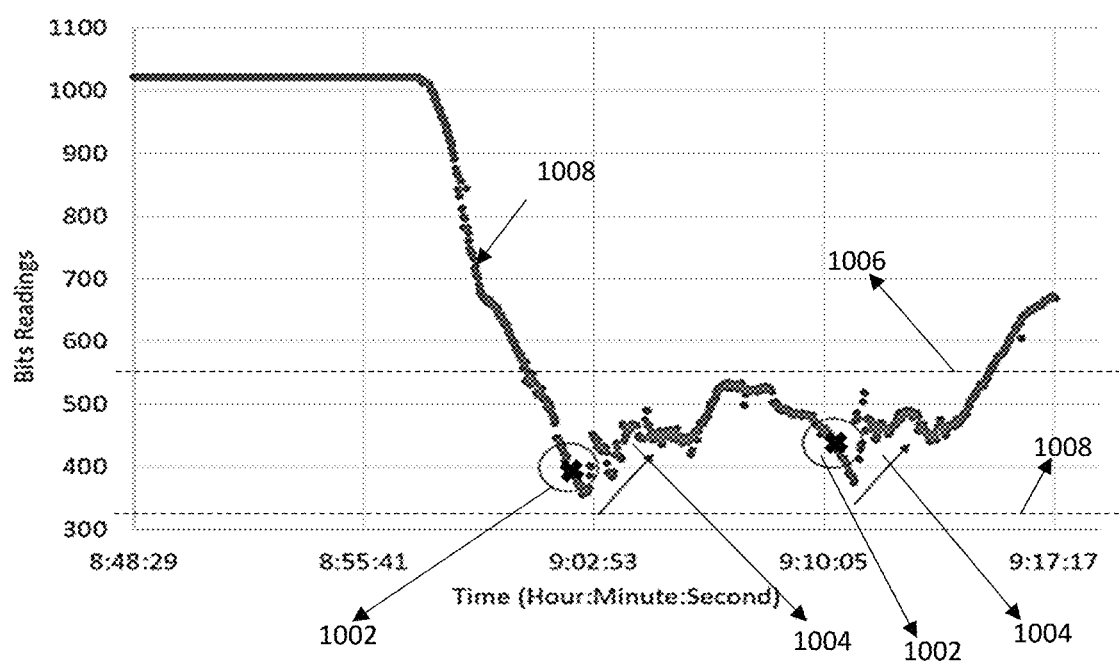
FIG. 10 depicts a graph of data collected that illustrates a Nil Per Os (NPO) test with the different water intakes during the workout.

FIG. 10 depicts a graph of data collected that illustrates a Nil Per Os (NPO) test with the different water intakes during the workout. The graph of FIG. 10 is of data collected that illustrates a nil per os (NPO) or nothing by mouth test with the different water intakes during the workout. Data was being gathered through nil per os (NPO) or nothing by mouth testing. The user or subject did not drink or eat anything at least 8 hours' prior to the test.

The graph, according to an embodiment, shows the real time data where x-axis represents the time in Hour: Minute: Seconds format and y-axis represents the data measurement in bits or number of binary digits that represent a digital number that represent a voltage. During the first 10 minutes of the workout (i.e., from 8:48:29 to 8:58:29) the user's body started perspiring as depicted by the fall in hydration by 1008. The fall in hydration level is a function of a person's parameters such as height, weight, age, etc., the activity the person is undertaking and the environmental conditions under which the person is undertaking such activity. Every dot represents a data measurement in bits or numbers of binary digits that represent a voltage. This voltage can be converted to a salt, electrolyte, or ion concentration value. As can be observed on the graph of FIG. 10, there are two water intakes on the subject's workout represented as cross marks highlighted by encircling the time region at which this event occurred as depicted by 1002. After these two water intakes one can observe how the hydration level of the user increases after 3 minutes i.e., segments of the graph represented as 1004. The algorithm producing the graph might have internal thresholds, for example, between 600 and 500 a line depicting 1006, where the device algorithm might alert the user or recommend to drink water. In another embodiment, another threshold can be made, where a hydration level below 300, then the user is alerted to drink water and probably stop the activity.

With this data an algorithm is created to create a strong correlation between the sweat of living beings and hydration status. This algorithm is introduced to the microcontroller to process the data received from the ion sensing circuit together with other sensing data such as heartbeat or using the data from other type of sensor(s) such as temperature, acetone sensor, gas sensor, atmospheric pressure sensor, GPS, accelerometer sensor and so on.

The Direct Current (DC) current is pulsed at a rate to prevent the accumulation of ions on the electrodes. Many factors are taken into account to optimize the pulsing frequency. In one embodiment of the present invention the DC current is pulsed at a maximum frequency of 200 Hz preferably operating at 100 Hz. The temperature of the users or the subject skin can also indicate a change in the user.

In one embodiment of the present invention, a temperature sensor is included in the ion sensing device to provide data related to hydration. In another embodiment of the invention, the microprocessor transmits the ion concentration status with a light that is red, yellow, or green depending on the hydration state of the user. In one embodiment, the device can be insulated to protect it from dust and water exposure. Also, the user can easily clean the device or switch the battery. All the data collected at the microprocessor can be sent through Bluetooth® to a smartphone or computer with software or a dedicated App. An App named hDrop is developed for collecting all the data from the device and analysing the data. Similar third-party apps compatible with the device can be developed and used in an embodiment. The data is further transferred and uploaded to a database and the user receives a graph of his or her workout from the real time data.

Another embodiment of the present invention is a device small enough to fit on a watch strap or a sports sleeve between other clothing apparel. With wireless technology, such as the current Bluetooth® connectivity or other commonly known wireless connection, the device is compatible with any wireless receiver, including an Apple Watch®, FitBit®, Garmin® watches, Polar® wearables and the like.

The method exploits a rectangular rounded design of the electrodes and a resistance measurement by a direct current pulsing signal. The conductive material of thin layer electrodes depicted in FIG. 2 as 204 and 206 are designed in a concentric manner and placed on a flexible substrate on one side which will be in contact with the skin and have an adhesive on the other side.

The circuit of the device is as illustrated in FIG. 6 includes a direct current source in electrical communication with a sensing circuit. The sensing circuit comprises a microcontroller 606, a first resistor R1 shown as 610 in electrical connection with the microcontroller, a capacitor C shown as 612 or a plurality of capacitors in series with the first resistor R1 shown as 610 or a plurality of resistors, and a second resistor R2 614 or a plurality of resistors is/are placed in parallel with the two or more electrodes and that is connected in series with the capacitor or the first capacitor in case of plurality of capacitors. After this last parallel connection between the last resistor or plurality of resistors and the electrodes 602, the circuit is connected to the microcontroller. The device may include more sensors such as a temperature sensor and a heart sensor and a readout for these sensors as well. The signals are processed in the microprocessor. The temperature sensor included on the flexible substrate is used for monitoring of the core body and/or skin temperature of the subject as well as in temperature correction of the resistance measurements from the circuit. The energy source may be remote or local, depending on whether the ion sensing device is portable or stationary and how the energy is transferred to the device. In one embodiment wherein the device is local, the energy source may consist of a coin cell lithium battery, a rechargeable battery, a renewable power source such as a solar cell or another type of energy harvester.

The device performs a resistance measurement based on an electrode measurement principle with a variable frequency from which the device can detect the electrolyte composition of a liquid by applying a pulsing direct current with a minimum time delay between each pulse of 10 ms. In order to detect different states of hydration of a person, a bit or the number of binary digits that represents the digital number that can be converted to an actual percentage of electrolyte concentration of a liquid. By knowing the electrolyte concentration of the liquid, in this case, sweat, the state of hydration can be determined using literature research values of the percentages of electrolytes in sweat. The current applied between the outer electrodes is a direct current (DC), which allows the extraction of all the information concerning the resistance equivalent circuit. Moreover, the ion sensing device and method allows the ion sensing circuit to contact the user's skin more easily than any other devices by using a two-dimensional flat electrode and obtaining a reading through a pulsating direct current in a delimited minimum amount of time. The design of the device allows sweat to constantly flow out of the measurement range of the electrodes so that new sweat is being analyzed constantly as soon as it is excreted from the body. In a preferred embodiment, the electrode is designed to be easily cleaned and reused for a long period of time. The ion sensing device may also be used to determine and monitor glucose levels in the user. A relationship that may be established between glucose and electrolyte concentration allows for the monitoring of glucose levels. A further embodiment of the present invention allows the creation of a non-invasive glucometer.

In one embodiment, the hydration monitoring system can be applied directly on the skin surface of a person and/or inside any type of wearable, such as a watch or a garment. The hydration monitoring system may be affixed on any type of flexible substrates on which thin conductive electrodes can be affixed or processed. Alternatively, the device may come in contact with the body fluid in any way, including but not limited to manual application.

Another embodiment shown in FIG. 9, wherein the system is encased in a protective housing with the sensing circuit positioned to appropriately contact the skin. The system is designed to wirelessly communicate with a smart hub serving as display interface and offers full information for hydration and also for some biological parameters characterizing body fluids and skin features. It can therefore be used for other classes of applications in health, sport and fitness exploiting these parameters.

The electrodes are configured to detect currents and/or voltages and determine the resistance differential between the electrodes when exposed to the fluid.

The microcontroller acts like a data pump by posting the data coming from the sensors. All this data can be obtained by a data acquisition hub, such as a personal smart hub which includes a nearby mobile device or a computer.

The voltage or current source is controlled and pulsed. The voltage is generated on the microcontroller or the main computer chip. This voltage is a low current, below 0.01 Amps, that allows the device to operate over direct skin without doing any damage to its user. This permits a safe environment for the user. The voltage is composed by a direct pulsing current. The voltage goes through the ion sensing circuit until it reaches the electrodes. When reaching the electrodes, the voltage goes through the liquid or semi-liquid surface that is in touch with the electrodes and travels through it, generating a certain voltage drop. This voltage drop is then converted into the hydration status by filtering it through an algorithm. By determining the peak voltage traveling through the circuit and the equivalent resistance, the voltage drop can be read on the reading node, previous to the resistor or plurality of resistors that are set in parallel with the electrodes.

An application of this device is to determine the electrolyte concentration over human skin between other applications. In order to zero out the skin resistance, the device can be applied on dry skin in order to determine the resistance value of the skin. The device may be optimized by asking the user a few questions through an App or questionnaire to determine the habits and body specifications of the user. The user will go through a calibration period. They will record some workouts (sedentary and active workouts) to determine the baseline of that specific user. Then a machine learning and/or a deep neural network will be used to generate the baseline of the user. After zeroing out the skin factor and taking into account factors such as: type of activity, exercise intensity, exercise duration, temperature, relative humidity, radiant heat/exposure, inside/outside air movement, clothing or wear, pre-exercise water intake, ability to replace fluids, electrolyte intake, level of heat acclimatization, body composition, age, fitness level, body temperature, heart rate, blood oxygen level, genetics among others. Using some or all of these parameters, an algorithm is created to determine the hydration status of the user.

Studies have shown that as the level of dehydration increases during exercise, various physiological functions are progressively impacted: heart rate and core temperature continually increase over time, while blood volume, stroke volume, cardiac output, and skin blood flow all decrease. For athletes, dehydration is the consequence of the thermal regulation of the body through sweating, which is a mix of water and minerals. In the most intensive effort, the quantity of water lost by the human body can overpass 3.5 litres. In case this loss of water and minerals is not compensated, dehydration can lead to hypovolemia (drop in blood pressure), hypokalaemia (paralysis of limbs), hyponatremia (breathing disorder, disorientation) and hypernatremia (too much sodium or electrolytes in blood).

These cases are extreme, but what is sure to be a consequence of dehydration is underperforming. Glucose is the gas of the body. Glycogen is made of three molecules of water. Thus, without water, an athlete will not be able to use its reserves of glucose. It is estimated that a water loss of 1% to 2% leads to a drop in performance of 10%.

Other populations to which the present invention is relevant are first responders and the fragile segments of the population, like the elderly and infants.

Figure 11:
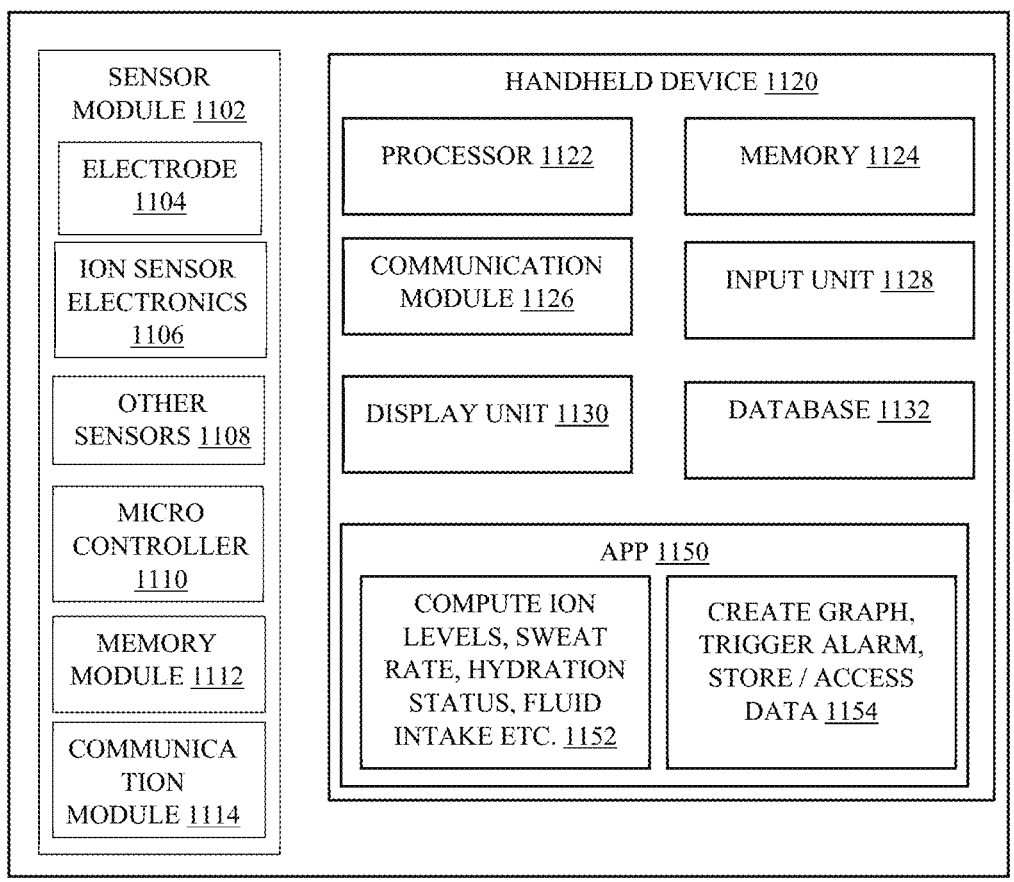
FIG. 11 depicts the sensor and other components and their interaction in the hand-held device according to an embodiment.

FIG. 11 depicts the sensor and other components and their interaction in the hand-held device according to an embodiment. It comprises a sensor module 1102 and a hand-held device 1120. The sensor module 1102 further comprises an electrode 1104, an ion sensor electronics 1106, and further may comprise other sensors such as temperature, heart rate sensor etc. It comprises a microcontroller 1110, a memory module 1112 and a communication module 1114 to communicate the data to the hand-held device 1112. The hand-held device comprises a processor 1122, memory 1124, a communication module 1126, an input unit 1128, a display unit 1130 and a database 1132. It may be interfaced with an App to computer ion levels, sweat rate, hydration status, fluid intake etc. at 1152. The App may further be programmed to create a graph in real time or post real time, an alarm and it is also used to store and access the data at 1154.

Figure 12:
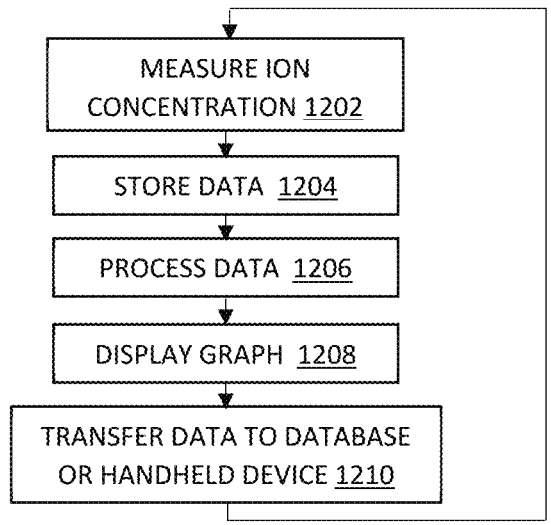
FIG. 12 depicts the process of measuring the ion concentration by the sensor of a device according to an embodiment.

FIG. 12 depicts the process of measuring the ion concentration by the sensor of the device according to an embodiment. The sensor of the device measures the ion concentration 1202, stores the data 1204, and processes the data at 1206. The data is further sent to display to produce a graph at 1208. The device may further be configured to transfer the data to a database or handheld device at 1210.

Figure 13:
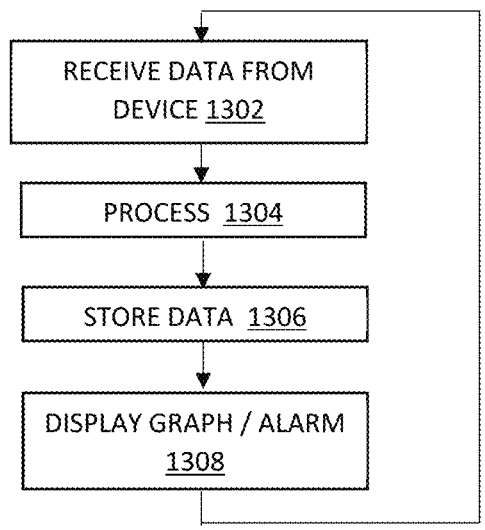
FIG. 13 depicts the process of communicating the data between the device and the server or display or to generate an alarm according to an embodiment.

FIG. 13 depicts the process of communicating the data between the device and the server or display or to generate an alarm according to an embodiment. The sensor uses its communication module to send the data to a database or a wearable or hand-held device having a display. The wearable device receives the data from device 1302, processes it at 1304, stores the data at 1306, and it can display graphs or give an alarm at 1308 depending on the configured algorithm in the app or the wearable or hand-held device.

EXAMPLES

The following examples pertain to further embodiments.

Experimental:

Experiment 1: A test was conducted to ensure the accuracy of the conductivity sensor, in a device, by conducting a simulation using a "drop" of sweat from a human.

Specific Technical Requirement(s) Intended to Verify:

The device detected changes of electrolyte concentration with 0.5 mL of sweat (ideally 50 µL).

The device reports an electrolyte concentration above 40 mmol/liter as dehydrated, below 30 mmol/liter as healthy and between these two as slightly dehydrated within 10% of expected value.

Equipment: A dropper (that can measure exactly 50 µL), a hydration monitoring device according to the present invention (fully assembled), pseudo arm or real arm, Container with 20 mL of 30 mmol/L NaCl concentration, Container with 20 mL of 40 mmol/L NaCl concentration Environment: The test was conducted in an Engineering Lab Test Method:
1. 50 µL of a 30 mmol/L concentration of NaCl solution was taken into the dropper.
2. The NaCl solution was placed on the finger skin of a human subject and spread to simulate sweating characteristics.
3. Ion sensing device was placed on top of the mixture on the finger to simulate the contact with the skin and keep the ion sensing circuit that functions as a sensor completely covered.
4. The average conductance was recorded at an average of 1-minute intervals.
5. Steps 1-4 were repeated with 40 mmol/L NaCl concentration.

Results

A finger was placed on top of the solution with equal force in order to compare to previous tests and keep the sensor completely covered.

TABLE 1

Conductivity readings for hDrop

| | 40 mmol/L NaCl | 30 mmol/L NaCl |
|---|---|---|
| Average Readings (most recent in Bits (Voltage), at 19.8° C.) | 493 | 562 |
| Resistance value | 18 kΩ | 23 kΩ |
| Original Values (in Bits, at 21.8° C.) | 663 | 700 |
| Resistance value | 32.5 kΩ | 37.3 kΩ |
| Percentage difference between both values based on bits) | 25.6% | 19.7% |

The process to convert the digital number represented by bits into resistance value is done by placing a known resistance value at the ends of the electrodes and comparing the resistance value with the number of bits recorded by the microcontroller. This permits the plot as depicted in FIG. 10 which illustrates the relationship between the digital values to resistance values according to an embodiment.

The original values were taken in an environment that was different from the readings above. This environment was at a different temperature and different relative humidity. Temperature affects the resistance value of the solution by a ±2% for each. The main reason the results differed is due to the temperature effect on conductance.

Ion Sensing Circuit or Sensor:

The ion sensing device comprises an electrode, which in one embodiment is a two-dimensional flat conductive printed electrode and the filtering and ion sensing circuit.

Two-Dimensional Flat Conductive Printed Electrode:

Using a two-dimensional flat conductive printed electrode, three main functions are accomplished. The whole sensor is in touch with the skin, and it can be easily customizable with a specific geometry for better results. The distance between the electrodes is fixed on this kind of electrode, which leads to more stable measurements. This kind of electrode is easy to clean and provides a long lifespan for the device. The device is configured using the information about the shape, area and distance of the electrode affecting the voltage drop for reading of data of the solution or electrolyte.

The factors of the shape and geometry of the electrode that could affect the microcontroller's analog to digital conversion and the voltage drop reading of the solution including the total area of the electrode and distance between the electrodes. If the area of the electrode increases, the resistance value decreases and if the distance between the electrodes increases, the resistance value increases.

Filtering and Sensing Circuit:

The filtering and sensing circuit shown in FIG. 6. follows the following process: The microcontroller sends pulses of DC current with a minimum time on/off of 5 ms, with a maximum frequency of 200 Hz. This frequency allows the electrons of the solution to reorganize to the initial salt structure before acquiring a reading. This effect is known as polarization that is avoided by applying pulses of direct current (DC) current. If the frequency pulse applied is greater than 100 Hz, the solution will start polarizing. The hydration monitoring device does not need an alternating current converter. The microcontroller applies the direct current pulses and creates an electric field. The electric field makes the ions move from one electrode to the other producing an ionic current. The device uses the Ohm's law to calculate the resistance value of the fluid sample. This resistance value can be converted to resistivity through the relationship between the area and length of the flat electrode in touch with the skin. The resistivity value can then be converted to conductivity and from that to salt or electrolyte concentration. This concentration is related to the hydration status of the user or the subject. By detecting the changes of those electrolytes, the device can monitor the hydration of the user wearing or using the device.

Additional factors that can affect the filtering and sensing circuit affecting the microcontroller's analog to digital conversion and the voltage drop reading of the solution are Cable resistance, Cable capacitance and Resistors and capacitors values Temperature Sensor:

In another embodiment, the hydration monitoring device includes a temperature sensor. The temperature sensor should be close to the skin in order to receive accurate readings. By using more than one temperature sensor, a calibration between the body temperature and the environment temperature can be done. Applying a layer of insulating or water proofing material around the temperature sensor and the internal circuit of the device allows it to protect the device. When applying this layer of insulating material, the effective temperature has to be recalculated in order to read accurate results from the temperature sensor. Conductivity is affected by temperature through the linear temperature coefficient as depicted in Equation (5).

$$C_{25} = \frac{C_t}{1 + \alpha(t - 25)} \quad \text{Equation (5)}$$

$C_{25}$ is the calculated conductivity at 25° C., Ct is the raw conductivity at t° C. (Centigrade), and a is the linear temperature coefficient. Just one temperature coefficient can be used with enough accuracy over a range of 30° C. or 40° C., accuracy can be improved by calculating a coefficient specifically for the sample temperature. This temperature variable affects the conductivity measurement and that is why there is a need to add a temperature sensor to the invention.

Microcontroller:

A Bluetooth Low Energy microcontroller has been used to control the sensors and pump data to a receiver hub, as defined herein above.

Data Collection and Analysis:

The invention's data collection is done through the microcontroller. The data obtained by the microcontroller is the millivolts reading converted bits from the Analog to Digital Converter (ADC) conversion as shown in the FIG. 10.

Many fluids in the human body contain electrolyte ions. These electrolytes ions (herein referred to as "electrolyte(s)") can conduct electricity in a solution, such as bodily fluids. One embodiment of the present invention is directed to an ion sensing device for measuring electrolytes in body fluids. Hydration, among other parameters, can be determined from the electrolyte concentration of a person.

The present invention is directed to a device comprising a microcontroller, a sensing circuit, and a voltage source. The microcontroller is affixed to a substrate and has a transmitter for transmitting the measurement of ions in the fluid. In one embodiment the transmitter for transmitting information to a receiver may be accomplished by a Bluetooth connection. The microcontroller is electrically connected to an ion sensing circuit also affixed to the substrate. The ion sensing circuit comprises a first resistor, a second resistor, a capacitor, two electrodes, a first node, a second node, and a reading node. The voltage source is affixed to the substrate and electrically connected to the microcontroller.

The capacitor is in series with the first resistor and electrically connected to a parallel connection having a second resistor; and two electrodes. The parallel connection is in series with the first resistor and the capacitor. The first node establishes an electrical connection between the capacitor and the parallel connection and is electrically connected to the reading node. The second node establishes an electrical connection between the capacitor and the parallel connection. The microcontroller is in electrical communication with the first node and electrical communication with the second node. The microcontroller pulses the voltage to the electrodes at a frequency such that polarization of the ions does not occur on the two electrodes; and wherein the reading node is connected to the transmitter.

The device calculates the difference between the electrolyte concentration in the fluid at different times and determines the hydration status of a user. The device measurements or the hydration status can be transmitted to a receiver to provide information to the user about the electrolyte composition of the fluid, including electrolyte concentrations, hydration or other information that may be useful to the user.

In another embodiment the flexible substrate is a wearable device or is affixed or embodied within a wearable. In a further embodiment the electrodes are two-dimensional electrodes that can be adjacent to the skin of the user and in contact with a sufficient amount of sweat, to allow topical monitoring. The receiver may be an iPhone or iPad, such as an App developed to receive information from the device, or other similar type of receiver.

Another embodiment of the present invention is directed to a method of measuring the electrolytes in a bodily fluid using the device described above. In another embodiment, the device is a wearable system that measures the hydration status of a user and informs the user.

A system for detecting salt ion concentration, comprising a device further comprising a sensor having a carbon printed electrode on a flexible substrate with adhesive on one side (backside) and the circuit electronics to generate pulse signal stimuli and measure salt concentrations to determine hydration level of a person or a living being, wherein the device is a wearable device.

The electrode can be made into different shapes changing the area as necessary, since it is a carbon printed electrode and is flexible.

The data can be processed at the same time on the microcontroller of the wearable device. The wearable device, further operable to send signals to a database. The database is configured for detecting the hydration level and sending an alert message.

These super thin, flexible sensors can also be used for chemical studies and experiments for calculating the ions and components for different chemical solutions. These can be embedded into either like a plastic case, or into a sock or a clothing piece.

A device, having an embedded algorithm that takes the measurements from a temperature sensor and a hydration sensor, and with the help of algorithm provides an accurate reading of hydration level of a person or a living being and further communicate that status and to a coach, to a parent, or to the concerned. When hydration drops below a certain point, a text, or a message to a trainer or to a coach who is monitoring a person to alert the need of water immediately.

This invention has three steps: a sensor, a combination of sensor and an algorithm and a database for monitoring and/or alerting.

A hardware device having a power input source and an embedded microcontroller, the circuit of the device comprising resistors and capacitors set up in a particular way or in a specific way to enable the device to work. The sensor is a carbon printed electrode which will be made to be in touch with the skin of a person or a living being. The sweat has ions and can conduct electricity through which the hydration levels can be measured.

When a constant current is applied through water having ions, electrolysis takes place and the resistance of water having ions will keep changing and the result cannot be accurate. Electrolysis of the salt solution impacts the signal that one is trying to generate. So, for a continuous monitoring system, the signal that one is trying to generate, i.e., the hydration signal in this case, will degrade over a period of time. Two things happening simultaneously, i.e., trying to measure the amount of salt, and having an electrolysis happening in the salt solution due to the stimuli for generating the measurement. Since, the idea is to generate the concentration of the salt and the hydration, it has to eliminate, to the extent possible, electrolysis due to the salt solution. The way this is achieved is by doing pulse measurement for the amount of salt. Pulse measurement is to measure for a fraction of a second and then turn off the stimuli. Instead of constantly monitoring by continuous current, a pulse current to generate the signal provides better and more accurate results. These pulse signals can be generated either by an electronic circuit, by software.

Therefore, the device generates pulses of current going through both electrodes and then the current goes through the sweat of a person or a living being and generates a constant reading of electrolytes in the sweating. Through the readings of the electrolytes information about start time of sweating, how long it takes to start sweating and the electrolytes levels can be found. Whenever a person drinks water, the body reacts to that after about three minutes, and then a different reading from the sensor.

The sensor is a super thin layer, flexible, with adhesive at the bottom surface to attach it easily to any device or any case or embodiment. The device can be placed on the arm of a person or a living being and who then can start his activity for example a run or a jog. There is also a temperature sensor that measures temperature as temperature and conductivity are related to each other. To calibrate the sensor, temperature reading of the whole duration or time of activity is needed. Once the readings are measured, all this data is then sent to an app through Bluetooth.

The app is compatible with Garmin® or any other wearable devices or watches. There is also an associated application (app/App) that is compatible with Android and iOS devices connected through Bluetooth. Once the device is connected via Bluetooth, the person or the living being can see the live status of their sweat, i.e., all the readings and the data. All this data is also sent to a server which creates a database. This data, on the database, is then processed, with a dedicated algorithm which also takes various other parameters of a person such as weight, height, etc., to find the accurate reading of hydration level for that person or living being.

Furthermore, the microcontroller and the software of the device can hold data for up to four hours but can be configured to hold as many hours of data as needed to hold. The sensor has a microcontroller which can work as a standalone device for measuring hydration levels. It is not required for a person to carry their phone while undergoing physical activity to monitor unless they wish to. They can carry this device alone. One can put it on their arm, and then you go for a physical activity. The device will store the data for four hours but can be configured for longer or shorter duration of storage of data. Whenever the device is reconnected with the phone, it will dump all the data into the phone. This sensor can be embedded into a device, for example, if a person has a Garmin® watch, they can connect the sensor and then go for a run with Garmin® which will enable them to see live data.

Once the sensor readings are obtained, they are converted into hashes, i.e., into a hash format, to make it into one long string, that is being sent from the microcontroller to the phone, then from the phone to the server. All this data in the server is stored in the hash format. For the analysis, the encrypted data is decrypted and then gets the readings.

In one embodiment, the pulse measurement is controlled by electronics and in another embodiment the pulse measurement is controlled by an external software.

There are other parameters which the device collects, such as age and weight. These factors are needed to be considered, because there are people that shed more salts and their sensors are to be calibrated accordingly. When the device recognizes that the electrolytes are less than they should be it identifies dehydration and then it will raise an alarm.

For example, during a workout, at the very beginning, a person may not sweat, so the measurement is zero. Then after like 10 to 15 minutes, the person may start sweating and hence the graph of hydration goes down indicating low levels of hydration. Whenever there is a water intake, after about three minutes, there is an increase in the hydration status, indicated by little peaks and marked by red arrows for identifying clear changes in the graph. The algorithm calculates the hydration levels and rehydration levels.

The excitation of pulsating direct current is pulsed at the predefined frequency is provided to prevent polarization of ions in the fluid across the pair of electrodes.

The ion sensing circuit determines ion concentration information of the fluid over time.

The micro-controller determines a physiological status of the subject based on the ion concentration information of the fluid over time.

The physiological status of the subject comprises at least one of a hydration status and a glucose status.

A database comprising conductivity information of at least one fluid of a subject, first ion concentration information of the at least one fluid obtained at a first instant, second ion concentration information of the at least one fluid obtained at a second instant, measurement information of at least one parameter of the subject such as age, weight, height etc., a plurality of environmental parameter that influences the reading of the sensor such as humidity, temperature, pressure, a location data with latitude, longitude and altitude information, a time stamp of date and time when the measurements happened or taken, and an index for a physiological status of a subject such as hydration level. The database further comprises user habits such as fluid intake, food intake etc.

In an embodiment, the device uses a carbon printed electrode to get hydration data from sweat placing it on top of the skin and the device is for a non-disposable, multi time use.

In an embodiment, the device uses pulsed frequency of DC current, with a frequency of no more than 200 Hz to measure electrolytes in sweat.

In an embodiment, the device comprises a flexible carbon printed electrode with adhesive on one side to be included on clothing, wearables.

In an embodiment, it is a system comprises a pair of electrodes, a temperature sensor and a data acquisition system or microcontroller to measure electrolyte concentration of sweat.

In an embodiment, it is a system comprised of a pair of electrodes, a temperature sensor and a data acquisition system or microcontroller to measure electrolyte concentration of sweat wherein a machine learning algorithm is used to determine user's hydration based on electrolyte levels, body temperature, weight, height, weather conditions obtained from live internet location data through the App, heartbeat, etc.

In an embodiment, it is a circuit to measure sweat conductivity comprises two resistors and one capacitor which makes the whole system a low-cost product.

In an embodiment, it is an add-on sensor for other existing wearable devices, able to transfer data through Bluetooth®.

In an embodiment, it is a device comprising, a sensor having a carbon printed electrode on a flexible substrate having an adhesive on one side; and an ion sensing circuit on the other side.

In an embodiment, it is a sensor comprising a carbon printed electrode on a flexible substrate having an adhesive on one side; and an ion sensing circuit on the other side.

In an embodiment, it is a sensor comprising a carbon printed electrode on a flexible substrate having an adhesive on one side; and an ion sensing circuit on the other side is made as a standalone device with or without a display.

In an embodiment, it is a device along with a database.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

U.S. Patent Application Publication 20160338639A1; U.S Patent Application Publication 20180263539A1, U.S. patent Ser. No. 10/092,203B2; U.S. Pat. No. 8,734, 341B2; U.S. Pat. No. 7,783,344B2; WO2016030869A1. All patents, patent application publications, and non-patent literature mentioned in the application are incorporated by reference in their entirety.

What is claimed is:

1. A device comprising:
a sensor comprising a pair of electrodes on a flexible substrate, the pair of electrodes comprising a first electrode and a second electrode; and
an ion sensing circuit;
wherein the pair of electrodes are arranged such that the first electrode is in proximity of the second electrode;
wherein the sensor is electrically connected to the ion sensing circuit comprising a microcontroller that generates a direct current pulse signal stimuli;
wherein the microcontroller only reads resistance using the direct current pulse signal stimuli; and
wherein the microcontroller is operable to determine ion concentration in a fluid of a subject based on the resistance.

2. The device of claim 1, wherein the ion sensing circuit further comprises:
at least a first resistor;
a capacitor electrically connected in series with the at least the first resistor;
at least a second resistor electrically connected in parallel with the pair of electrodes; and
a first node which is a reading node, electrically connected to the second resistor connected to a second node which is in parallel to the capacitor and the first resistor, wherein the reading node is configured to read an output signal from the sensor.

3. The device of claim 2, wherein the reading node is electrically connected to a transmitter.

4. The device of claim 1, wherein the device is operable to determine hydration level from detecting the ion concentration of the fluid of the subject, by measuring conductance of the fluid of the subject.

5. The device of claim 1, wherein the pair of electrodes are carbon printed 2D flexible flat electrodes and are configurable to different shapes.

6. The device of claim 1, wherein the pair of electrodes are carbon printed on one side of the flexible substrate with adhesive on another side of the flexible substrate.

7. The device of claim 1, wherein the pair of electrodes are operable to an area and a distance between the pair of electrodes wherein the area and the distance between the pair of electrodes can be varied.

8. The device of claim 1, wherein the microcontroller is operable to control an energy source and provide the direct current pulse signal stimuli.

9. The device of claim 1, wherein the device is wearable and portable.

10. The device of claim 1, wherein the device could be attached to a clothing item.

11. The device of claim 1, wherein the direct current pulse signal stimuli are in a frequency range from 0 to 200 Hertz.

12. The device of claim 1, wherein the device further comprises a wireless communication circuit that is operable to perform wireless transmission and reception.

13. The device of claim 12, wherein the wireless communication circuit supports wireless connectivity comprising one selected from a Bluetooth, a Wi-Fi, an RFID, a BLE, a Radio Frequency Signal, and GSM.

14. The device of claim 1, wherein the subject comprises one of a living being and a non-living being.

15. The device of claim 1, wherein the fluid comprises any fluid that contains electrolytes.

16. The device of claim 1, wherein the ion sensing circuit is operable to detect a conductivity of the fluid in real time.

17. The device of claim 1, wherein the pair of electrodes is in non-invasive contact with the subject.

18. The device of claim 1, wherein the sensor is operable to measure at least one parameter of the subject that impacts ion concentration of the fluid.

19. The device of claim 1, wherein the pair of electrodes are arranged in a concentric manner.

20. A sensor comprising:
a pair of electrodes on a flexible substrate, the pair of electrodes comprising a first electrode and a second electrode; and
an ion sensing circuit comprising:
a microcontroller;
at least a first resistor;
a capacitor electrically connected in series with the first resistor;
at least a second resistor electrically connected in parallel with the pair of electrodes;
a first node which is a reading node, electrically connected to the second resistor connected to a second node which is in parallel to the capacitor and the first resistor, wherein the reading node is configured to read an output signal from the sensor;
wherein the microcontroller generates a direct current pulse signal stimuli;
wherein the pair of electrodes are arranged such that the first electrode is in proximity of the second electrode;
wherein the sensor only reads resistance using the direct current pulse signal stimuli; and
wherein the sensor is operable to detect ion concentration in a fluid of a subject based on the resistance.

21. A system comprising:
a sensor comprising:
a pair of electrodes on a flexible substrate, the pair of electrodes comprising a first electrode and a second electrode; and an ion sensing circuit comprising:
a microcontroller;
at least a first resistor;
a capacitor electrically connected in series with the at least the first resistor;
at least a second resistor electrically connected in parallel with the pair of electrodes;
a first node which is a reading node, electrically connected to the second resistor connected to a second node which is in parallel to the capacitor and the first resistor, wherein the reading node is configured to read an output signal from the sensor;
wherein the sensor is electrically connected to the ion sensing circuit comprising the microcontroller that generates a direct current pulse signal stimuli;
wherein the sensor is operable for detecting ion concentration in a fluid of a subject;
wherein the pair of electrodes are arranged such that the first electrode is in proximity of the second electrode;
wherein the sensor only reads resistance using the direct current pulse signal stimuli; and
wherein the sensor communicates through a wireless communication with a second system comprising at least a processor, a memory in communication with the processor, a communication module, a display, and a database.

* * * * *